(12) United States Patent
Aydin

(10) Patent No.: US 10,195,417 B2
(45) Date of Patent: Feb. 5, 2019

(54) CONNECTING ELEMENT FOR PROVIDING FLUIDIC CONNECTION BETWEEN VESSELS

(71) Applicant: Parker Hannifin Manufacturing Germany GmbH & Co. KG, Bielefeld (DE)

(72) Inventor: Tolga Aydin, Bad Wimpfen (DE)

(73) Assignee: PARKER HANNIFIN MANUFACTURING GERMANY GMBH & CO. KG, Bielefeld (DE)

( * ) Notice: Subject to any disclaimer, the term of this patent is extended or adjusted under 35 U.S.C. 154(b) by 0 days.

(21) Appl. No.: 15/487,637

(22) Filed: Apr. 14, 2017

(65) Prior Publication Data

US 2017/0266430 A1    Sep. 21, 2017

Related U.S. Application Data

(62) Division of application No. 14/501,434, filed on Sep. 30, 2014, now Pat. No. 9,636,494.

(30) Foreign Application Priority Data

Oct. 2, 2013    (DE) .................. 10 2013 220 073

(51) Int. Cl.
*A61M 39/26*    (2006.01)
*F16L 37/30*    (2006.01)
*A61M 39/10*    (2006.01)

(52) U.S. Cl.
CPC ............ *A61M 39/26* (2013.01); *A61M 39/10* (2013.01); *F16L 37/30* (2013.01); *A61M 2039/262* (2013.01); *Y10T 137/87933* (2015.04)

(58) Field of Classification Search
CPC ........ A61M 39/26; A61M 39/10; F16L 37/30; Y10T 137/87933
See application file for complete search history.

(56) References Cited

U.S. PATENT DOCUMENTS

| | | |
|---|---|---|
| 4,421,296 A | 12/1983 | Stephens |
| 5,535,785 A | 7/1996 | Werge et al. |
| 5,901,942 A | 5/1999 | Lopez |
| 6,170,800 B1 | 1/2001 | Meloul et al. |
| 7,296,782 B2 | 11/2007 | Enerson et al. |
| 9,636,494 B2 * | 5/2017 | Aydin .................. A61M 39/26 |

(Continued)

FOREIGN PATENT DOCUMENTS

| | | |
|---|---|---|
| DE | 40 26 524 A1 | 3/1992 |
| DE | 10 2010 047 747 A1 | 4/2012 |

(Continued)

OTHER PUBLICATIONS

European Search Report, Appl. No. 14186337.3, dated Feb. 6, 2015, 5 pgs.

(Continued)

*Primary Examiner* — Kevin Lee
(74) *Attorney, Agent, or Firm* — Paul D. Strain, Esq.; Strain & Strain PLLC

(57) ABSTRACT

The application relates to a connecting element, in particular for connecting vessels and for producing a fluidic connection between vessels or elements joined to the connecting element. The invention also relates to an elastic spring element as a valve element.

40 Claims, 7 Drawing Sheets

(56) References Cited

U.S. PATENT DOCUMENTS

| | | |
|---|---|---|
| 2007/0007478 A1 | 1/2007 | Leinsing et al. |
| 2010/0108681 A1 | 5/2010 | Jepson et al. |
| 2015/0090353 A1 | 4/2015 | Aydin |

FOREIGN PATENT DOCUMENTS

| | | |
|---|---|---|
| JP | 2004-257521 A | 9/2004 |
| WO | WO 98/11931 A1 | 3/1998 |
| WO | WO 2006/078355 A1 | 7/2006 |
| WO | WO 2009/111596 A2 | 9/2009 |
| WO | WO 2010/111546 A2 | 9/2010 |

OTHER PUBLICATIONS

German Search Report, Appl. No. 10 2013 220 073.0, dated Feb. 28, 2014, 5 pgs.
Aydin, U.S. PTO Office Action, U.S. Appl. No. 14/501,434, dated Jul. 27, 2016, 11 pgs.
Aydin, U.S. PTO Office Action, U.S. Appl. No. 14/501,434, dated Oct. 5, 2016, 5 pgs.
Aydin, U.S. PTO Restriction Requirement, U.S. Appl. No. 14/501,434, dated Feb. 24, 2016, 5 pgs.
Aydin, U.S. PTO Notice of Allowance, U.S. Appl. No. 14/501,434, dated Dec. 29, 2016, 5 pgs.

* cited by examiner

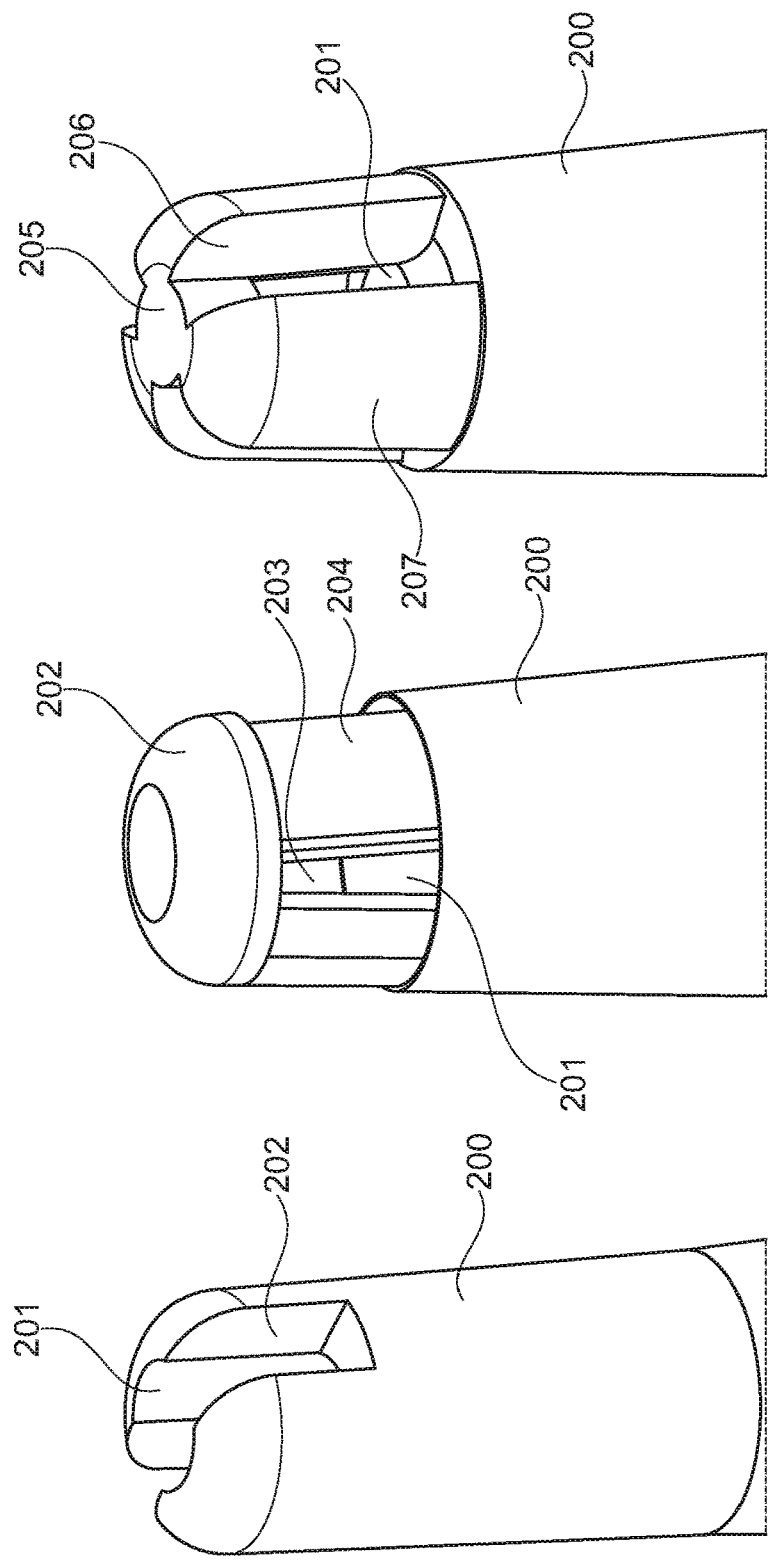

CONNECTING ELEMENT FOR PROVIDING FLUIDIC CONNECTION BETWEEN VESSELS

CROSS-REFERENCE TO RELATED PATENT APPLICATIONS

This application is a Divisional of U.S. application Ser. No. 14/501,434, filed Sep. 30, 2014, now U.S. Pat. No. 9,636,494, which is based upon and claims the benefit of priority from prior German Patent Application No. 10 2013 220 073.0, filed Oct. 2, 2013, the entire contents of which are incorporated herein by reference in their entirety.

TECHNICAL FIELD

The invention relates to a connecting element, in particular for connecting vessels and for producing a fluidic connection between vessels or elements joined to the connecting element. The invention also relates to an elastic spring element as a valve element.

PRIOR ART

In particular in the medical sphere of use, it is known in the prior art that liquid solutions or drugs are collected from a storage vessel by means of syringes and administered to patients. For this purpose, it is known that the liquid is collected by the syringe directly via the hollow needle of the syringe and is subsequently administered directly to the patient.

It is also known that a connecting element is placed onto the storage vessel, and the syringe can then be attached to said connecting element in order to draw the liquid out of the storage vessel into the syringe. When the syringe is subsequently pulled out therefrom again, liquid can still escape from the syringe, which is highly disadvantageous in particular in the case of very expensive drugs. Soiling is therefore also possible because escaping drugs or liquids may be lost, and this is considered to be disadvantageous in the medical sphere or in the care sphere.

It is also known that infusion solutions in particular can be connected to a hollow needle by means of tube lines, wherein drugs can also be metered into such tube lines or hollow needles. This then takes place via a connecting element which is subject to the same disadvantages as already described above.

SUMMARY OF THE INVENTION, OBJECT, SOLUTION, ADVANTAGES

It is the object of the invention to provide a connecting element which permits a secure connection and, nevertheless, if nothing is connected thereto, permits a secure and tight closure of the vessel connected thereto. It is also the object of the invention to provide an elastic spring element as the valve element, which permits secure sealing with a simultaneous simple design.

This is achieved by the features of claim 1.

An advantageous exemplary embodiment of the invention relates to a connecting element with a housing having a first receiving space with a first joining element and a first shiftable valve element arranged therein, and having a second receiving space with a second joining element with a second shiftable valve element arranged therein, the first and the second receiving space are fluidically connected to each other, wherein the first valve element is of elastically deformable design and is shiftable, and the second valve element is of elastically deformable design and is shiftable, wherein the first valve element is shiftable between two positions, wherein, in the first position, a fluidic connection between the first receiving space and the first joining element is interrupted by the first valve element and, in the second position, a fluidic connection between the first receiving space and the first joining element is opened by the first valve element, and wherein the second valve element is shiftable between two positions, wherein, in the first position, a fluidic connection between the second receiving space and the second joining element is interrupted by the second valve element and, in the second position, a fluidic connection between the second receiving space and the second joining element is opened by the second valve element, wherein the first valve element is formed with a duct which is closed in the first position of the first valve element and is opened in the second position of the first valve element, wherein a hollow pin is arranged in the first receiving space and engages in the duct. A connecting element which is sealed on both sides is thereby provided.

The object is also achieved by the features of claim 2.

An exemplary embodiment of the invention relates to a connecting element with a housing having a first receiving space with a first joining element and a first shiftable valve element arranged therein, and having a second receiving space, the first and the second receiving space are fluidically connected to each other, wherein the first valve element is of elastically deformable design and is shiftable, wherein the first valve element is shiftable between two positions, wherein, in the first position, a fluidic connection between the first receiving space and the first joining element is interrupted by the first valve element and, in the second position, a fluidic connection between the first receiving space and the first joining element is opened by the first valve element, wherein the first valve element is formed with a duct which is closed in the first position of the first valve element and is opened in the second position of the first valve element, wherein a hollow pin is arranged in the first receiving space and engages in the duct. A connecting element which is sealed on one side is thereby provided.

According to the invention, the housing is of at least two-part design, wherein the at least two housing parts are advantageously connected to each other, for example, in particular, are connected to each other so as not to be releasable nondestructively. The at least two parts here can be, for example, welded or adhesively bonded to one another. If more than two housing parts are connected to one another, said housing parts can be welded to one another. It is also possible for only some of said housing parts to be welded to one another. It is possible for other housing parts merely to be inserted or adhesively bonded.

Furthermore, it is advantageous if the first receiving space and the second receiving space are formed by a first and a second housing part, wherein the first housing part form the first receiving space and the second receiving space, wherein the second housing part bounds the first receiving space in the manner of a cover. The second housing part here is preferably a type of cover which is placed onto the other, first housing part and closes off or bounds a receiving space.

It is particularly advantageous if the hollow pin is inserted as a third housing part into the first or the second housing part. The hollow pin can thus be inserted with a retaining plate into one of the receiving spaces and can optionally be connected to the housing part.

It is particularly advantageous if the third housing part forming the hollow pin is connected in an integrally bonded manner to the first or the second housing part. The third housing part here can be connected to one of the other housing parts.

Alternatively, it is also advantageous if the hollow pin is formed integrally with the first or the second housing part, for example, in particular, is injected molded thereon. The installation complexity can thereby be reduced.

It is also advantageous if the first joining element is arranged or formed on the first housing part and the second joining element is arranged or formed on the second housing part. This has the effect that the two joining elements can lie opposite each other if the respective housing parts are correspondingly designed. This achieves a simple flow therethrough.

It is also advantageous if the first receiving space has a circular cross section in section and is bounded by an encircling wall, wherein the receiving space is bounded by two approximately flat, in particular upper and lower, wall regions, wherein the first joining element is arranged or accommodated on one of the two walls, in particular the upper wall, and a fluidic connection to the second receiving space is provided in the other wall, in particular the lower wall.

It is also advantageous if the first receiving space has a circular cross section in section with outwardly protruding pockets and is bounded by an encircling wall which is changeable in radius, wherein the receiving space is bounded by two approximately planar wall regions, such as, in particular, an upper and lower wall, wherein the first joining element is arranged or accommodated on one of the two walls, in particular the upper wall, and a fluidic connection to the second receiving space is provided in the other wall, in particular the lower wall. The design of the pockets permits the simple arrangement of spring arms of the valve element. As a result, the position of the spring arms is relatively well defined and a secure arrangement of the spring arms is ensured even under application of force.

It is particularly advantageous if the number of pockets is greater than or equal to the number of spring arms of a valve element inserted into the receiving space.

It is particularly advantageous if a spring arm of the valve element is arranged in each pocket. The bearing of the spring arms is thereby unambiguously defined and no errors with regard to erroneous insertion can occur even during the installation.

It is also advantageous if the first joining element has a hollow-cylindrical element and the first valve element has at least one cylindrical region which is accommodated in a shiftable manner in the hollow-cylindrical element. The cylindrical element here serves for sealing off or opening up an opening in the joining element.

Furthermore, it is advantageous if the first valve element has spring arms protruding at the cylindrical region. The valve element can thereby be shifted counter to the restoring force of the spring arms.

It is particularly advantageous here if the spring arms protrude from the cylindrical region in a manner substantially corresponding to the edges of a tetrahedron. A secure positioning of the spring arms and therefore of the valve element is thereby achieved.

It is also expedient if the protruding spring arms are designed as spring arms which are rectilinear or are kinked or curved once or multiple times. In the case of the curved or kinked spring arms, a defined spring deflection is achieved by bending about a predetermined bending point.

It is particularly advantageous if the spring arms of the first valve element are arranged at an angle of 120° to one another in the plane perpendicular to the longitudinal axis of the cylindrical region.

It is also advantageous here if the spring arms have a first region which is arranged at an angle of approximately 25 to 30°, preferably 27°, to the plane perpendicular to the longitudinal axis of the cylindrical region.

It is also advantageous if the spring arms have a second region which is arranged at an angle of approximately 35 to 40°, preferably 37°, to the plane perpendicular to the longitudinal axis of the cylindrical region.

Furthermore, it is advantageous if the spring arms have a third region which is arranged at an angle of approximately 75 to 80°, preferably 77°, to the plane perpendicular to the longitudinal axis of the cylindrical region.

An advantageous defined bending behavior under load is achieved by the multiple kinking.

It is particularly advantageous if, in the event of a load being applied to the cylindrical region, the spring arms are deformed in an arcuate manner such that the cylindrical region substantially carries out an axial movement.

According to the invention, it is expedient if the duct of the valve element is open on one side and is designed to be closeable on the opposite side with a closeable and openable slot. A slot here is, for example, a longitudinal slot or a cross- or star-shaped slot or a slot formed in some other way.

It is advantageous here if, in the unloaded state of the valve element, the hollow pin only partially engages, if at all, in the duct and does not act upon the slot in the closed state, and therefore the duct is closed.

It is also advantageous if, in the loaded state of the valve element, the hollow pin virtually completely engages in or reaches through the duct and acts upon or pushes through the slot, and therefore the duct is opened.

According to the invention, it is expedient if the second joining element has a hollow-cylindrical element.

It is advantageous if the second joining element has a hollow-cylindrical element and the second valve element has at least one cylindrical region which is accommodated in a shiftable and/or deformable manner in the hollow-cylindrical element. By means of an application of force to the second valve element, the latter can be shifted and/or deformed in a receptacle of the second joining element in order to open or to close a fluidic connection.

It is advantageous here if the second valve element has spring arms protruding at the cylindrical region. The second valve element can thereby is shiftable counter to the restoring force of the spring arms. The second spring element is also elastically deformable because of its inherent elasticity counter to the restoring force.

It is advantageous here if the spring arms protrude from the cylindrical region in a manner substantially corresponding to the edges of a tetrahedron.

The protruding spring arms can also be designed as spring arms which are rectilinear or are kinked or curved once or multiple times.

It is particularly advantageous if the spring arms of the second valve element are arranged at an angle of 120° to one another in the plane perpendicular to the longitudinal axis of the cylindrical region.

Furthermore, it is advantageous if the spring arms have a first region which is arranged inclined at an angle of approximately 35 to 55°, in particular approximately 45°, to the plane perpendicular to the longitudinal axis of the cylindrical region.

It is also advantageous if the spring arms have a second region which is arranged in a plane perpendicular to the longitudinal axis of the cylindrical region.

Furthermore, it is advantageous if, in the event of a load being applied to the cylindrical region, the spring arms are deformed in an arcuate manner such that the cylindrical region substantially carries out an axial movement.

It is also advantageous if the cylindrical region of the second valve element bends under a load. As a result, the second cylindrical region can lift off from a sealing surface of the second receiving space and open up a fluidic connection.

It is also expedient if the end side of the second receiving space has a radially inwardly directed constriction against which the second valve element is positioned in a sealing manner in the unloaded state.

The object is also achieved by the features of claim 36.

An exemplary embodiment of the invention relates to an elastic spring element with a cylindrical body and spring arms protruding therefrom, wherein the spring element is manufactured from an elastic material.

It is advantageous here if the protruding spring arms are designed as spring arms which are kinked and/or curved once or multiple times.

It is also expedient if the spring arms of the first and/or second valve element are arranged at an angle of 120° to one another in the plane perpendicular to the longitudinal axis of the cylindrical region.

It is expedient here if the spring arms have a first region which is arranged at an angle of approximately 35 to 55° to a plane perpendicular to the longitudinal axis of the cylindrical region.

It is also advantageous if the spring arms have a second region which is arranged in a plane perpendicular to the longitudinal axis of the cylindrical region.

It is also advantageous if the cross section of the spring arm is of round or oval or polygonal design.

It is also advantageous if the cross section of the spring arm is oval, wherein the cross section has a smaller diameter in a plane through the mean perpendicular of the spring element than in the direction perpendicular thereto.

It is also advantageous if the cylindrical body has an encircling sealing lip or an encircling sealing region at an end region which is arranged opposite the spring arms.

It is also advantageous if the sealing lip or the sealing region is designed as an encircling step.

Further advantageous refinements are described by the description below of the figures and by the dependent claims.

BRIEF DESCRIPTION OF THE DRAWINGS

The invention is explained in more detail below on the basis of at least one exemplary embodiment and with reference to the drawings, in which:

FIG. 14 shows a perspective view of an opening in the hollow pin, FIG. 15 shows a perspective view of an opening in the hollow pin, FIG. 16 shows a perspective view of an opening in the hollow pin.

PREFERRED EMBODIMENT OF THE INVENTION

Figure 1:
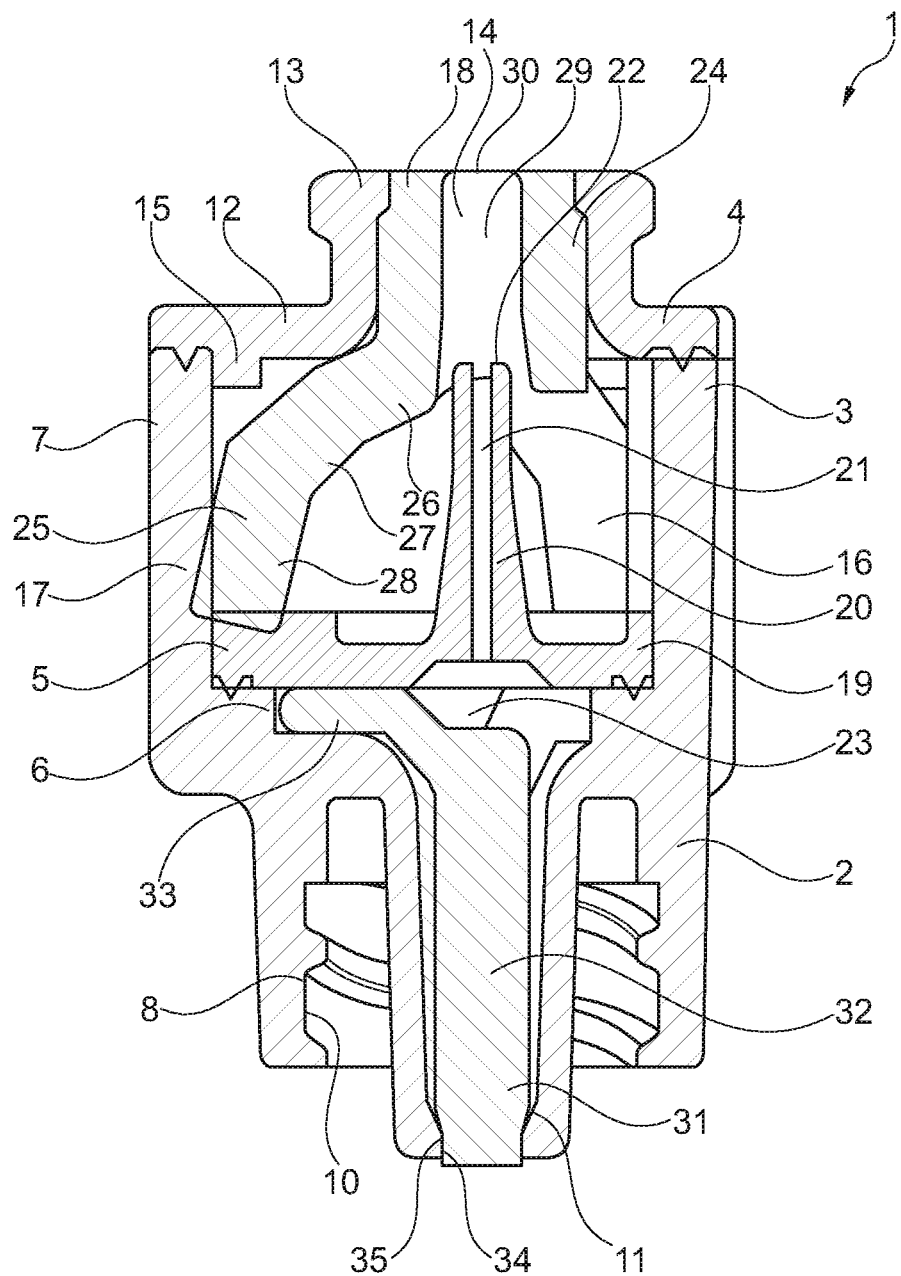
FIG. 1 shows a section of a first exemplary embodiment of a connecting element according to the invention.
Figure 6:
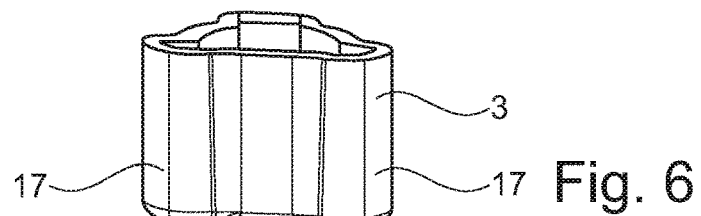
FIG. 6 shows a perspective view of a housing part.
Figure 7:
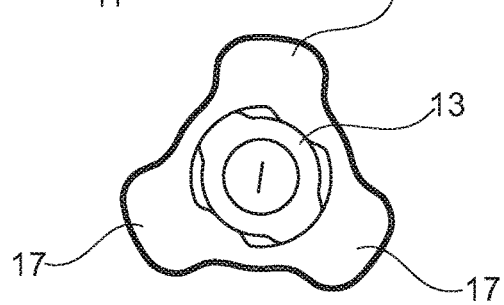
FIG. 7 shows a view of the connecting element from above.

FIGS. 1 to 7 show a first exemplary embodiment of a connecting element 1 according to the invention in various illustrations. FIG. 1 shows the connecting element 1 in section, FIGS. 2 to 6 show an exploded illustration in a perspective view, and FIG. 7 shows a top view.

The connecting element 1 is designed with a housing 2. The housing 2 consists of at least two housing parts, wherein three housing parts 3, 4, 5 are provided in this exemplary embodiment. The housing parts 3, 4 are formed connected to each other, for example welded to each other. The housing part 5 is inserted into the housing part 3 and is also connected there to the housing part 3.

The first housing part 3 has a base 6 with an encircling wall 7 protruding at an angle of 90° thereon. The wall 7 here is oriented substantially axially.

The base 5 is provided with the joining element 8. For this purpose, the joining element 8 is attached as a joining branch to the base 6. Said joining element is advantageously connected or formed integrally with the base 6. An element which is to be connected can be connected here for example screwed, to the joining element 8. For this purpose, a thread 10 is provided by means of which the element to be connected can be screwed.

The housing part 3 has a tubular region 11 which protrudes in the axial direction from the base 6 and protrudes from the base 6 in the opposite direction to the wall 7.

Figure 2:
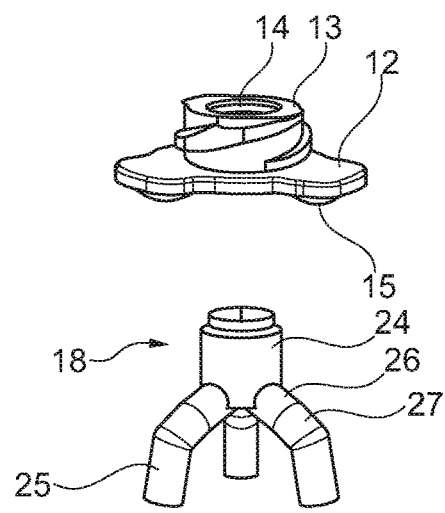
FIG. 2 shows a perspective view of a housing part.
Figure 3:
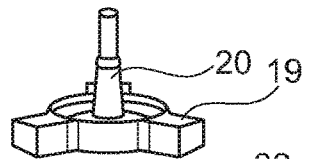
FIG. 3 shows a perspective view of a valve element.
Figure 4:
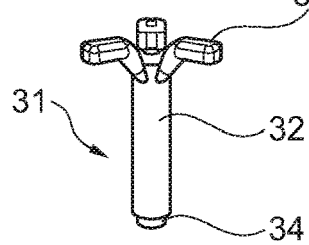
FIG. 4 shows a perspective view of a housing part.
Figure 5:
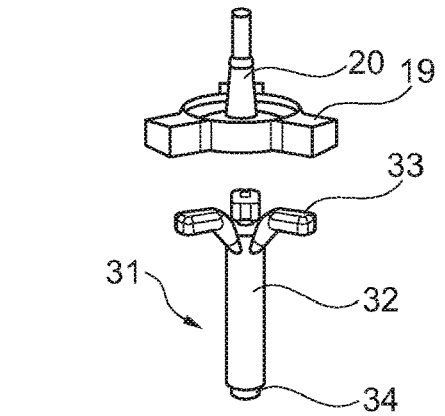
FIG. 5 shows a perspective view of a valve element.

The second housing part 4 is formed in the manner of a cover with a base 12, from which a joining branch 13 with a fluid opening 14 extends upward in the axial direction. A projection 15 which engages radially on the inside and in the axial direction in the wall 7 is provided in the opposite direction. As illustrated in FIG. 2, the projection 15 is designed in a segmented manner and distributed over the circumference of the base 12.

As can be seen in FIG. 1, the two housing parts 3, 4 are connected to each other, for example welded, on the end side of the wall 7. Alternatively, adhesive bonding, pressing together, clipping, etc. may also be usable.

The housing 2 forms a first receiving space 16, wherein said receiving space is arranged within the housing part 3 in the region closed off from the housing part 4. The receiving space 16 here is surrounded by the wall 7.

According to FIGS. 1 and 6, the wall 7 is not of completely round design, but rather has pockets 17 which protrude radially outward and serve for receiving spring arms of the valve element. The pockets 17 here are designed as radially outwardly protruding regions of a circle, wherein the radius of the wall 7 is smaller between the pockets 17.

The third housing part 5 is arranged in the receiving space 16. Said housing part has a baseplate 19 and a hollow pin 20 which protrudes therefrom and has a continuous duct 21. At the upper end of the hollow pin, the pin has two opposite projections 22 which allow the duct to end therebetween in a manner running in the lateral direction. The duct 21 is open toward the second receiving space 23.

Furthermore, a valve element 18 is arranged in the receiving space 16.

The joining element 13 is provided upward on the base 12 of the housing part 4, as already described above. If an element to be connected to the joining element 13, such as, for example, a syringe or similar, or a branch attached thereto, is inserted or screwed into the joining element 13, fluidic communication between the element to be connected and the receiving space 16 is intended to be able to take place. If an element to be connected is not inserted into the joining element 13, the joining element 13 is intended to be closed off and sealed.

This is achieved by the valve element 18. The valve element 18 has a cylindrical region 24 from which spring arms 25 protrude downward. The cylindrical region 24 with the spring arms 25 is advantageously formed integrally here and the spring arms 25 protrude radially outward and downward from the cylindrical region 24 at an angle of approximately 45° to the vertical. When three spring arms are present, the spring arms 25 approximately form an arrangement in accordance with an edge arrangement of a tetrahedron.

The protruding spring arms 25 are advantageously designed as spring arms 25 which are rectilinear or are kinked or curved once or multiple times. In the exemplary embodiment of FIGS. 1 to 6, the spring arms 25 are designed to be kinked twice.

For this purpose, the spring arms 25 have a first region 26 which is arranged at an angle α1 of approximately 25 to 30°, preferably 27°, to the plane perpendicular to the longitudinal axis of the cylindrical region 24.

Furthermore, the spring arms 25 have a second region 27 which is arranged at an angle α2 of approximately 35 to 40°, preferably 37°, to the plane perpendicular to the longitudinal axis of the cylindrical region 24.

The spring arms also have a third region 28 which is arranged at an angle α3 of approximately 75 to 80°, preferably 77°, to the plane perpendicular to the longitudinal axis of the cylindrical region 24.

The cylindrical region 24 has a duct 29 which is closed at its upper end. The cylindrical region 24 has there a slot 30 which opens when deformed.

If the slot 30 is closed, a fluidic connection between the joining element 13 and the receiving space 16 is prevented. If the slot 30 is opened, a fluidic connection between the joining element 13 and the receiving space 16 is made possible.

If the valve element 18 is pressed downward in the axial direction by an element to be connected, the hollow pin 20 engages in the duct 29 and deforms the cylindrical region 24 such that the slot is opened.

In the positions of the valve element 15 that are shown in FIG. 1, a fluidic connection between the joining element 13 and the receiving space 16 is closed off and sealed. If an element is inserted from above into the joining element 13, the cylindrical region 24 of the valve element 18 is compressed and pushed downward, and therefore the spring arms 25 are supported on the edges of the pockets 17 and are elastically deformed. The cylindrical region 24 is thereby shifted downward and the fluidic connection is made possible by means of slot 30 and duct 29 and the hollow pin.

If the element to be connected is removed again from the joining element 7, the elastic moldable valve element 18 relaxes again and the cylindrical region 24 is pushed upward again, and therefore the joining element 13 is sealed again.

The interior of the connecting element 1 is divided by the base 19. The receiving space 23 which is of approximately cylindrical design is arranged below the base 19. The second valve element 31 with the cylindrical region 32 and the spring arms 33 is arranged in said receiving space 23. The spring arms are arranged between a flank of the first housing part and the base 19 and support the cylindrical region 32 in the axial direction. If an element to be connected is screwed into the joining region 8, the cylindrical region 32 of the second valve element is shifted axially upward counter to the restoring force of the spring arms 33, with the cylindrical region 32 also being deformed. In the process, the lower sealing region 34 is released from the encircling bead 35 of the tubular region 11 and a fluid flow is permitted.

Preferably, the elastic elements which are provided as valve elements 18, 31 consist of an elastomeric material and the housing elements 3, 4, 5 consist of a non-elastomeric, but rather dimensionally stable, material, such as of thermoplastic. The element 18 and the element 31 here can preferably be composed of liquid silicone rubber (LSR) or silicone rubber crosslinking at a high temperature (HTC) or silicone rubber crosslinking at room temperature (RTC), and the housing parts 3, 4, 5 can consist of acrylonitrile/butadiene/styrene (ABS), polycarbonate (PC), polypropylene (PP) or polyethylene (PE) or the like.

Figure 8:
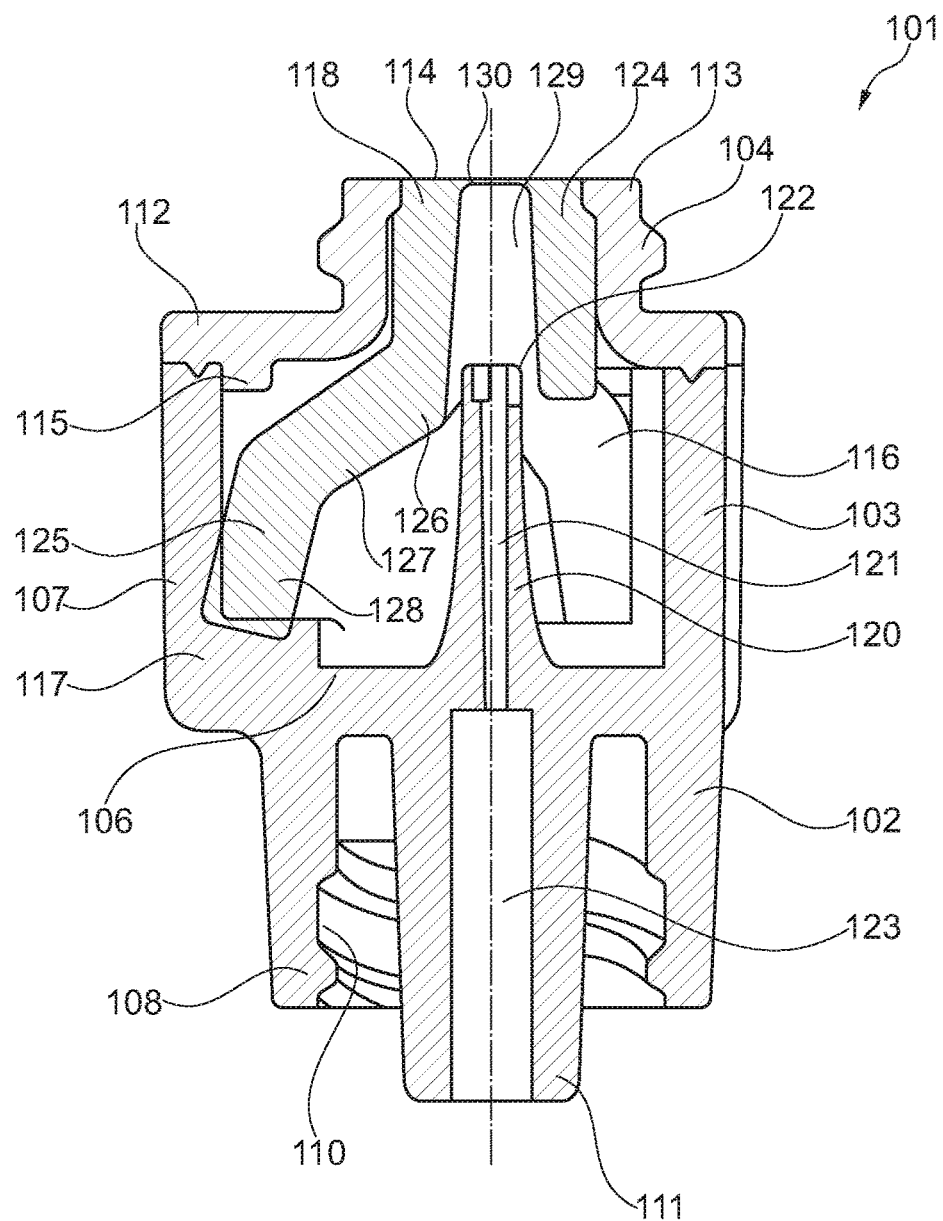
FIG. 8 shows a section of a second exemplary embodiment of a connecting element according to the invention.
Figure 9:
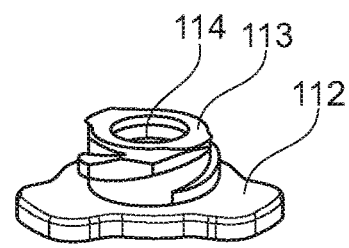
FIG. 9 shows a perspective view of a housing part.
Figure 10:
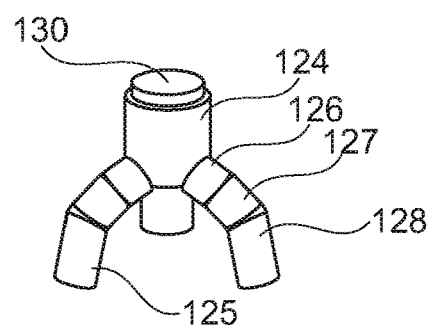
FIG. 10 shows a perspective view of a valve element.
Figure 11:
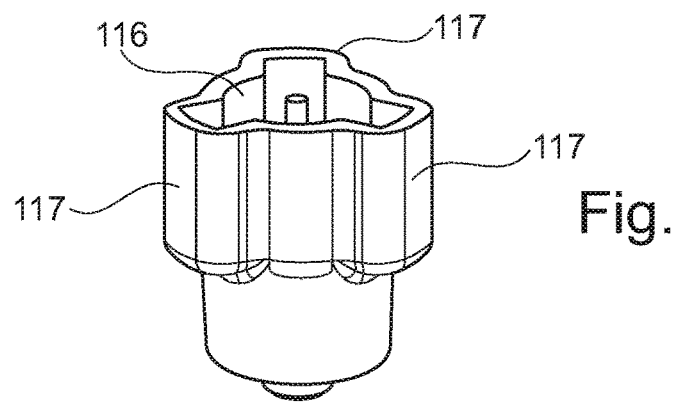
FIG. 11 shows a perspective view of a housing part.
Figure 12:
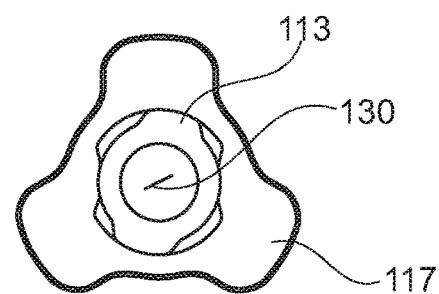
FIG. 12 shows a view of the connecting element from above.

FIGS. 8 to 12 show a second exemplary embodiment of a connecting element 101 according to the invention in various illustrations. FIG. 8 shows the connecting element 101 in section, FIGS. 9 to 11 show an exploded illustration in a perspective view, and FIG. 12 shows a top view.

The connecting element 101 is designed with a housing 102. The housing 102 consists of at least two housing parts 103, 104. The housing parts 103, 104 are formed connected to each other, for example welded to each other. Instead of an additional housing part, the hollow pin is formed integrally with the housing part 103 in this exemplary embodiment.

The first housing part 103 has a base 106 with an encircling wall 107 protruding at an angle of 90° thereon. The wall 107 here is oriented substantially axially.

The base 105 is provided with the joining element 108. For this purpose, the joining element 108 is attached to the base 106 as a joining branch. Said joining element is advantageously connected or formed integrally with the base 106. An element which is to be connected can be connected here, for example screwed, to the joining element 108. For this purpose, a thread 110 is provided by means of which the element to be connected can be screwed.

The housing part 103 has a tubular region 111 which protrudes in the axial direction from the base 106 and protrudes from the base 106 in the opposite direction to the wall 107.

The second housing part 104 is designed in the manner of a cover with a base 112, from which a joining branch 113 with a fluid opening 114 extends upward in the axial direction. A projection 115 is provided in the opposite direction, said projection engaging radially on the inside and in the axial direction into the wall 107. As illustrated in FIG. 9, the projection 115 is designed in a segmented manner and distributed over the circumference of the base 112.

As can be seen in FIG. 8, the two housing parts 103, 104 are connected to each other, for example welded, on the end side of the wall 107. Alternatively, adhesive bonding, pressing together, clipping, etc. may also be usable.

The housing 102 forms a first receiving space 116, wherein said receiving space 116 is arranged within the housing part 103 in the region closed off from the housing part 104. The receiving space 116 is surrounded here by the wall 107.

According to FIGS. 8 and 11, the wall 107 is not of completely round design, but rather has radially outwardly protruding pockets 117 which serve for receiving spring arms of the valve element. The pockets 117 here are designed as radially outwardly protruding regions of a circle, wherein the radius of the wall 107 is smaller between the pockets 117.

A hollow pin 120 which protrudes from the base 106 and has a continuous duct 121 is accommodated in the receiving space 116. At the upper end of the hollow pin, the pin has two opposite projections 122 which allow the duct to end therebetween in a manner running in the lateral direction. The duct 121 is opened toward the second receiving space 123.

Furthermore, a valve element 118 is arranged in the receiving space 116.

The joining element 113 is provided upward on the base 112 of the housing part 104, as already described above. If an element to be connected to the joining element 113, such as, for example, a syringe or the like, or a branch attached thereto, is inserted or screwed into the joining element 113, fluidic communication between the element to be connected and the receiving space 116 is intended to be able to take place. If an element to be connected is not inserted into the joining element 113, the joining element 113 is intended to be closed off and sealed.

This is achieved by the valve element 118. The valve element 118 has a cylindrical region 124 from which spring arms 125 protrude downward. The cylindrical region 124 with the spring arms 125 is advantageously of integral design here and the spring arms 125 protrude radially outward and downward from the cylindrical region 124 at an angle of approximately 45° to the vertical. When three spring arms are present, the spring arms 125 approximately form an arrangement in accordance with an edge arrangement of a tetrahedron.

The protruding spring arms 125 are advantageously designed as spring arms 125 which are rectilinear or are kinked or curved once or multiple times. In the exemplary embodiment of FIGS. 8 to 12, the spring arms 125 are designed to be kinked twice.

For this purpose, the spring arms 125 have a first region 126 which is arranged at an angle α1 of approximately 25 to 30°, preferably 27°, to the plane perpendicular to the longitudinal axis of the cylindrical region 124.

Furthermore, the spring arms 125 have a second region 127 which is arranged at an angle α2 of approximately 35 to 40°, preferably 37°, to the plane perpendicular to the longitudinal axis of the cylindrical region 124.

The spring arms also have a third region 128 which is arranged at an angle α3 of approximately 75 to 80°, preferably 77°, to the plane perpendicular to the longitudinal axis of the cylindrical region 124.

The cylindrical region 124 has a duct 129 which is closed at its upper end. The cylindrical region 124 there has a slot 130 which opens when deformed.

If the slot 130 is closed, a fluidic connection between the joining element 113 and the receiving space 116 is prevented. If the slot 130 is opened, a fluidic connection between the joining element 113 and the receiving space 116 is made possible.

If the valve element 118 is pressed downward in the axial direction by an element to be connected, the hollow pin 120 engages in the duct 129 and deforms the cylindrical region 124, and therefore the slot is opened.

In the positions of the valve element 118 that are shown in FIG. 8, a fluidic connection between the joining element 113 and the receiving space 116 is closed off and sealed. If an element is inserted from above into the joining element 113, the cylindrical region 124 of the valve element 118 is compressed and pushed downward such that the spring arms 125 are supported on the edges of the pockets 117 and are elastically deformed. As a result, the cylindrical region 124 is shifted downward and the fluidic connection is made possible by means of slot 130 and duct 129 and the hollow pin.

If the element to be connected is removed again from the joining element 107, the elastic moldable valve element 118 is relaxed again and the cylindrical region 124 is pushed upward again, and therefore the joining element 113 is sealed again.

The interior of the connecting element 101 is divided by the base 106. The receiving space 123, which is of approximately cylindrical design, is arranged below the base 106. A valve element is not arranged in said receiving space 123. If an element to be connected is screwed into the joining region 106, there is a fluidic connection to the receiving space 116.

Preferably, the elastic element which is provided as valve element 118 consists of an elastomeric material and the housing elements 3, 4 consist of a non-elastomeric, but rather dimensionally stable, material, such as thermoplastic. The element 118 here can preferably consist of liquid silicone rubber (LSR) or silicone rubber crosslinking at a high temperature (HTC) or silicone rubber crosslinking at room temperature (RTC), and the housing parts 3, 4 can consist of acrylonitrile/butadiene/styrene (ABS), polycarbonate (PC), polypropylene (PP) or polyethylene (PE) or the like.

Figure 13:
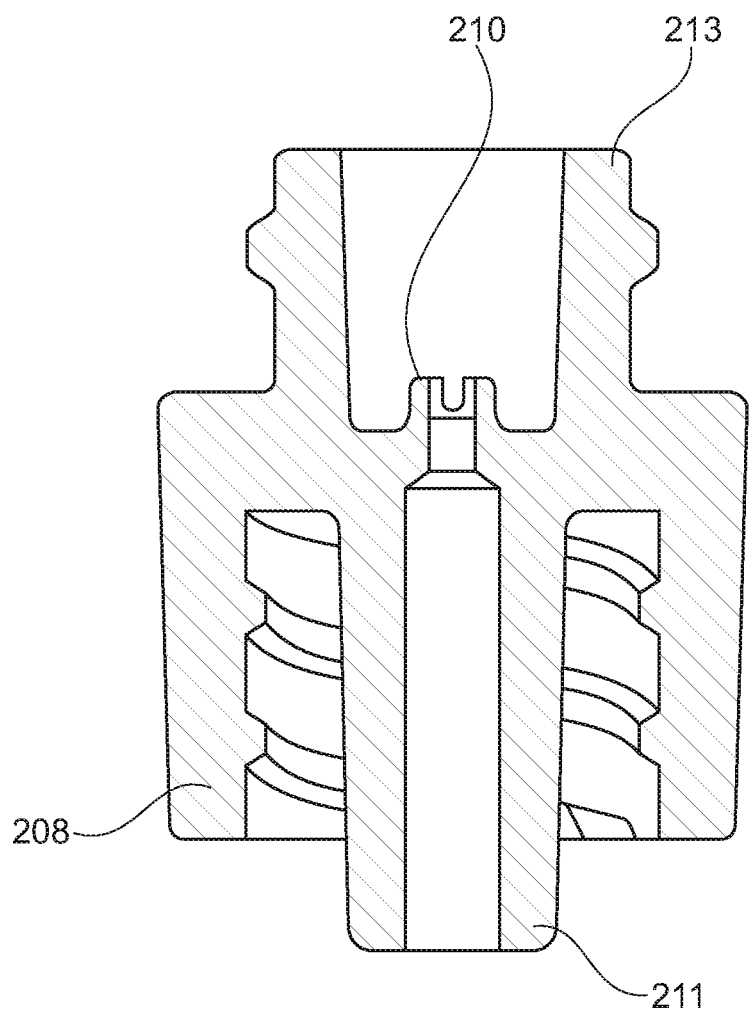
FIG. 13 shows a perspective view of an adapter element.

FIG. 13 shows a connecting element 201 which serves as an adapter part. It connects the joining elements 213 and 208 to the tubular element 211, as are also already known from the previous figures, wherein no valve elements are provided in this exemplary embodiment. If the joining element 213 is screwed into the joining element 8 of FIG. 1, the second valve element is acted upon in the axial direction by the projection 210 and the fluidic connection is opened by shifting and deformation of the second valve element.

An arrangement of a connecting element 1 with a connecting element 101 in a series connection is conceivable. In this case, an element to be connected (which cannot, however, be seen) is screwed from above onto the joining region 13. As a result, the cylindrical element 24 is shifted downward and the spring arms 25 are braced in an arcuate manner. The connecting element 1 is screwed here from above onto the connecting element 101, and therefore the joining region 8 is screwed onto the joining region 113. As a result, the cylindrical element 124 is shifted downward and the spring arms 125 are braced in an arcuate manner. The second connecting element 32 is likewise acted upon by the hollow pin 20 and deformed and shifted. There is a fluidic connection from the joining element 13 as far as the joining element 118.

FIGS. 14 to 16 each show the upper end of the hollow pin 200, in which the opening differs in design in each case. In FIG. 14, the hollow pin 200 has a cylindrical duct 201 which has by a slit formation 202 provided transversely to the orientation of the duct, and therefore the opening in the duct not only takes place upward, but also to the side.

In FIG. 15, the hollow pin 200 has a cylindrical duct 201 which is covered at its end by a cap 202, wherein openings 203 for the discharge of the fluid are formed laterally and below the cap. The openings 203 are spaced apart from one another by webs 204.

In FIG. 16, the hollow pin 200 likewise has a cylindrical duct 201 which is covered at its end by a cap 205, wherein openings 206 for the discharging of the fluid are formed laterally and extending upward into the cap. The openings 206 are spaced apart from one another by webs 207.

Figure 17:
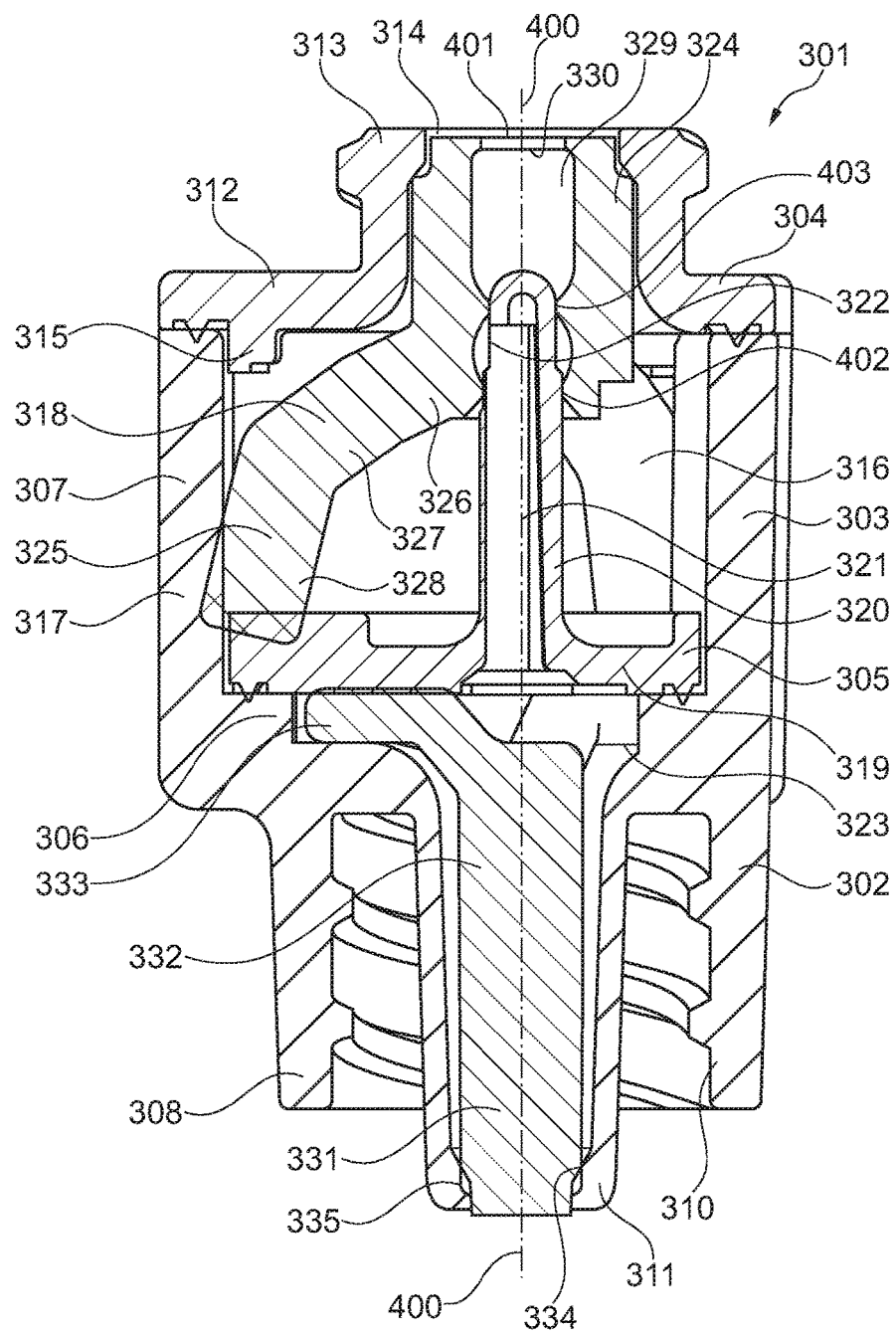
FIG. 17 shows a section of a further exemplary embodiment of a connecting element according to the invention.

FIG. 17 shows a further exemplary embodiment of a connecting element 301 according to the invention in section.

The connecting element 301 is designed with a housing 302. The housing 302 consists of at least two housing parts, wherein three housing parts 303, 304, 305 are provided in this exemplary embodiment. The housing parts 303, 304 are formed connected to each other, for example welded or adhesively bonded to each other. The housing part 305 is inserted into the housing part 303 and is also optionally connected there to the housing part 303. Alternatively, the connection of the housing part 303 to the housing part 305 can also be dispensed with, as could correspondingly also be the case with the other exemplary embodiments. As the connection, adhesive bonding, welding or clamping or an interlocking connection could be possible in all of the examples.

The first housing part 303 has a base 306 with an encircling wall 307 protruding thereon at an angle of 90°. The wall 307 here is oriented substantially axially. This means that the wall is oriented in the axial direction to the center axis 400, for example parallel thereto.

The base 305 is provided with the joining element 308. For this purpose, the joining element 308 is attached to the base 306 as a joining branch. Said joining element is advantageously connected or formed integrally with the base 306. An element to be connected can be connected, for example, screwed, here to the joining element 308. For this purpose, a thread 310 is provided by means of which the element to be connected can be screwed.

The housing part 303 has a tubular region 311 which protrudes from the base 306 in the axial direction and protrudes from the base 306 in the opposite direction to the wall 307.

The tubular region 311 is arranged radially within the joining element 308 and is embraced by the latter. The tubular region 311 also protrudes out of the joining element 308 in the axial direction.

The second housing part 304 is formed in the manner of a cover with a base 312, from which a joining branch 313 with a fluid opening 314 extends upward in the axial direction, i.e. away from the receiving space 316 which forms a chamber. A projection 315 is provided in the opposite direction, said projection engaging radially on the inside and in the axial direction into the wall 307. The projection 315 is advantageously designed in a segmented manner and is distributed over the circumference of the base 312 or alternatively is also of encircling design.

As can be seen in FIG. 17, the two housing parts 303, 304 are connected to each other, for example welded, on the end side of the wall 307. Alternatively, adhesive bonding, pressing together, clipping, etc. may also be useable.

The housing 302 forms a first receiving space 316, wherein said receiving space is arranged within the housing part 303 in the region closed off from the housing part 304. The receiving space 316 here is surrounded by the wall 307.

According to FIG. 17 and corresponding to FIGS. 6, 7, 11 and 12, the wall 307 is not of completely round design but rather has radially outwardly protruding pockets 317 which serve for receiving spring arms of the valve element. The pockets 317 are designed as radially outwardly protruding regions of a circle, wherein the radius of the wall 307 is smaller between the pockets 317.

The third housing part 305 is arranged in the receiving space 316. Said housing part has a baseplate 319 and a hollow pin 320 which protrudes therefrom and has a continuous duct 321. At the upper end of the hollow pin, the hollow pin 320 has a type of cap, wherein an opening 322 is provided laterally in order to allow fluid to flow in or out. The duct 321 is open toward the second receiving space 323.

Furthermore, a valve element 318 is arranged in the receiving space 316.

The joining element 313 is provided upward on the base 312 of the housing part 304, as already described above. If an element to be connected to the joining element 313, such as, for example, a syringe or the like, or a joining branch attached thereto, is inserted or screwed into the joining element 313, a fluidic communication is intended to be able to take place between the element to be connected and the receiving space 316. If an element to be connected is not inserted into the joining element 313, the joining element 13 is intended to be closed off and sealed.

This is achieved by the valve element 318. The valve element 318 has a cylindrical region 324 from which spring arms 325 protrude downward. The cylindrical region 324 here is advantageously formed integrally with the spring arms 325 and the spring arms 325 protrude radially outward and downward from the cylindrical region 324 at an angle of approximately 45° to the vertical. If three spring arms 325 are present, the spring arms 325 approximately form an arrangement in accordance with an edge arrangement of a tetrahedron.

The protruding spring arms 325 are advantageously designed as spring arms 325 which are rectilinear or are kinked or curved once or multiple times. In the exemplary embodiment of FIG. 17, the spring arms 325 are designed to be kinked twice.

For this purpose, the spring arms 325 have a first region 326 which is arranged at an angle $\alpha 1$ of approximately 25 to 30°, preferably 27°, to the plane perpendicular to the longitudinal axis 400 of the cylindrical region 324.

Furthermore, the spring arms 325 have a second region 327 which is arranged at an angle $\alpha 2$ of approximately 35 to 40°, preferably 37°, to the plane perpendicular to the longitudinal axis 400 of the cylindrical region 324. The spring arms also have a third region 328 which is arranged at an angle $\alpha 3$ of approximately 75 to 80°, preferably 77°, to the plane perpendicular to the longitudinal axis 400 of the cylindrical region 324.

The cylindrical region 324 has a duct 329 which is closed at its upper end by a wall formation 401. The cylindrical region 324 has there a slot 330 which opens when the wall formation 401 is deformed.

If the slot 330 is closed, a fluidic connection between the joining element 313 and the receiving space 316 is prevented. If the slot 330 is opened, a fluidic connection between the joining element 313 and the receiving space 316 is made possible.

If the valve element 318 is pressed downward in the axial direction by an element to be connected, the hollow pin 320 engages in the duct 329 and deforms the cylindrical region 324 such that the slot is opened.

FIG. 17 shows that the duct 329 is of substantially cylindrical or conical design and extends in the axial direction. On its inner circumference, the duct 329 has two radially inwardly protruding annular sealing lips 402, 403 or sealing beads. Said sealing lips 402, 403 protrude radially inward and bear against the hollow pin 320 and seal off the latter. It can be seen in FIG. 17 that the sealing lip 403 is arranged above the opening 322 and the sealing lip 402 is arranged below the opening, and therefore the two sealing lips 402, 403 are arranged on both sides, as viewed in the axial direction, of the opening 322 in the hollow pin.

As an alternative to the two sealing lips 402, 403, it is also possible for only one such sealing lip to be provided, or it is also possible for more than two such sealing lips to be provided.

In the positions of the valve element 315 that are shown in FIG. 17, a fluidic connection between the joining element 313 and the receiving space 316 is closed off and sealed. If an element is inserted from above into the joining element 313, the cylindrical region 324 of the valve element 318 is compressed and/or pushed downward such that the spring arms 325 are supported on the edges of the pockets 317 and are elastically deformed. As a result, the cylindrical region 324 is shifted downward and the fluidic connection is made possible by means of slot 330 and duct 329 and the hollow pin.

If the element to be connected is removed again from the joining element 307, the elastic moldable valve element 318 relaxes again and the cylindrical region 324 is pushed upward again, and therefore the joining element 313 is sealed again.

The interior of the connecting element 301 is divided by the base 319. The receiving space 323 which is of approximately cylindrical design is arranged below the base 319. The second valve element 331 with the cylindrical region 332 and the spring arms 333 is arranged in said receiving space 23. The spring arms are arranged between a flank of the first housing part and the base 319 and support the cylindrical region 332 in the axial direction. If an element to be connected is screwed into the joining region 308, the cylindrical region 332 of the second valve element is shifted upward axially counter to the restoring force of the spring arms 333, wherein the cylindrical region 332 is also deformed. In the process, the lower sealing region 334 is released from the encircling bead 335 of the tubular region 311 and a fluid flow is permitted.

Preferably, the elastic elements which are provided as valve elements 318, 331 consist of an elastomeric material and the housing elements 303, 304, 305 consist of a nonelastomeric, but rather dimensionally stable, material, such as of thermoplastic. The element 318 and the element 331 here can preferably consist of liquid silicone rubber (LSR) or silicone rubber crosslinking at a high temperature (HTC) or silicone rubber crosslinking at room temperature (RTC), and the housing parts 303, 304, 305 can consist of acrylonitrile/butadiene/styrene (ABS), polycarbonate (PC), polypropylene (PP) or polyethylene (PE) or the like.

The invention claimed is:

1. A connecting element comprising:
    a first receiving space having a first valve element arranged therein, wherein the first valve element interrupts connection between a first joining element and the first receiving space and comprises an elastically deformable component, wherein the first valve element is configured to operate in two positions, wherein, in the first position, a fluidic connection between the first receiving space and the first joining element is interrupted by the first valve element and, in the second position, a fluidic connection between the first receiving space and the first joining element is opened by the first valve element,
    a second receiving space having a second valve element arranged therein, wherein the second valve element interrupts connection between a second joining element and the second receiving space and comprises an elastically deformable component, wherein the second valve element is configured to operate in two positions, wherein, in the first position, a fluidic connection between the second receiving space and the second joining element is interrupted by the second valve element and, in the second position, a fluidic connection between the second receiving space and the second joining element is opened by the second valve element.

2. The connecting element according to claim 1, wherein the first valve element is formed with a duct which is closed in the first position of the first valve element and is opened in the second position of the first valve element, wherein a hollow pin is arranged in the first receiving space and engages in the duct.

3. The connecting element according to claim 1, further comprising a housing having at least two housing parts, wherein the at least two housing parts are connected to each other so as not to be releasable nondestructively.

4. The connecting element according to claim 3, wherein the first receiving space and the second receiving space are formed by a first and a second housing part, wherein the first housing part forms the first receiving space and the second receiving space, wherein the second housing part bounds the first receiving space on one side.

5. The connecting element according to claim 4, wherein the hollow pin is inserted as a third housing part into the first or the second housing part.

6. The connecting element according to claim 5, wherein the third housing part is connected in an integrally bonded manner to the first or the second housing part.

7. The connecting element according to claim 6, wherein the hollow pin is formed integrally with the first or the second housing part and is injection molded thereon.

8. The connecting element according to claim 1, wherein the first joining element has a hollow-cylindrical element and the first valve element has a cylindrical region which is accommodated in a shiftable manner in the hollow-cylindrical element.

9. The connecting element according to claim 8, wherein the first valve element has spring arms protruding at the cylindrical region.

10. The connecting element according to claim 9, wherein the first receiving space has outwardly protruding pockets, wherein ends of the spring arms of the first valve element are arranged in the outwardly protruding pockets.

11. The connecting element according to claim 10, wherein the protruding spring arms are spring arms which are rectilinear or are kinked or curved once or multiple times.

12. The connecting element according to claim 9, wherein, in the event of a load being applied to the cylindrical region, the spring arms are deformed in an arcuate manner such that the cylindrical region substantially carries out an axial movement.

13. The connecting element according to claim 1, wherein the duct of the first valve element is open on one side and is closeable on the opposite side with a closeable and openable slot.

14. The connecting element according to claim 2, wherein, in an unloaded state of the first valve element, the hollow pin does not act upon the slot in the closed state, and therefore the duct is closed.

15. The connecting element according to claim 2, wherein, in a loaded state of the first valve element, the hollow pin virtually completely engages in or reaches through the duct and acts upon or pushes through the slot, and therefore the duct is opened.

16. The connecting element according to claim 1, wherein the second joining element has a hollow-cylindrical element.

17. The connecting element according to claim 1, wherein the second joining element has a hollow-cylindrical element and the second valve element has a cylindrical region which is accommodated in a shiftable and/or deformable manner in the hollow-cylindrical element.

18. The connecting element according to claim 17, wherein the second valve element has spring arms protruding at the cylindrical region.

19. The connecting element according to claim 18, wherein the protruding spring arms are spring arms which are rectilinear or are kinked or curved once or multiple times.

20. The connecting element according to claim 18, wherein the spring arms have a second region which is arranged in a plane perpendicular to a longitudinal axis of the cylindrical region.

21. The connecting element according to claim 18, wherein, in the event of a load being applied to the cylindrical region, the spring arms are deformed in an arcuate manner such that the cylindrical region substantially carries out an axial movement.

22. The connecting element according to claim 18, wherein the cylindrical region of the second valve element bends under a load.

23. The connecting element according to claim 2, wherein the first valve element has, on the duct, at least one radially inwardly protruding sealing lip which can be positioned on the hollow pin for sealing purposes.

24. The connecting element according to claim 2, wherein the first valve element comprises an elastic spring element with a cylindrical body and spring arms protruding therefrom, wherein the spring element is manufactured from an elastic material.

25. The connecting element according to claim 24, wherein the protruding spring arms are spring arms which are kinked or curved once or multiple times.

26. The connecting element according to claim 24, wherein the spring arms have a region which is arranged in a plane perpendicular to a longitudinal axis of the cylindrical region.

27. A connecting element comprising:
a first receiving space having a first valve element arranged therein, wherein the first valve element interrupts connection between a first joining element and the first receiving space and comprises an elastically deformable component, wherein the first valve element is configured to operate in two positions, wherein, in the first position, a fluidic connection between the first receiving space and a first joining element is interrupted by the first valve element and, in the second position, a fluidic connection between the first receiving space and the first joining element is opened by the first valve element, wherein the first valve element is formed with a duct which is closed in the first position of the first valve element and is opened in the second position of the first valve element, wherein a hollow pin is arranged in the first receiving space and engages in the duct, and
a second receiving space fluidically connected to the first receiving space.

28. The connecting element according to claim 27, further comprising a housing having at least two housing parts, wherein the at least two housing parts are connected to each other so as not to be releasable nondestructively.

29. The connecting element according to claim 28, wherein the first receiving space and the second receiving space are formed by a first and a second housing part, wherein the first housing part forms the first receiving space and the second receiving space, wherein the second housing part bounds the first receiving space on one side.

30. The connecting element according to claim 29, wherein the hollow pin is inserted as a third housing part into the first or the second housing part.

31. The connecting element according to claim 30, wherein the third housing part is connected in an integrally bonded manner to the first or the second housing part.

32. The connecting element according to claim 31, wherein the hollow pin is formed integrally with the first or the second housing part and is injection molded thereon.

33. The connecting element according to claim 27, wherein the first joining element has a hollow-cylindrical element and the first valve element has a cylindrical region which is accommodated in a shiftable manner in the hollow-cylindrical element.

34. The connecting element according to claim 33, wherein the first valve element has spring arms protruding at the cylindrical region.

35. The connecting element according to claim 34, wherein the first receiving space has outwardly protruding pockets, wherein ends of the spring arms of the first valve element are arranged in the outwardly protruding pockets.

36. The connecting element according to claim 35, wherein the protruding spring arms are spring arms which are rectilinear or are kinked or curved once or multiple times.

37. The connecting element according to claim 36, wherein, in the event of a load being applied to the cylindrical region, the spring arms are deformed in an arcuate manner such that the cylindrical region substantially carries out an axial movement.

38. The connecting element according to claim 27, wherein the duct of the first valve element is open on one side and is closeable on an opposite side with a closeable and openable slot.

39. The connecting element according to claim 38, wherein, in an unloaded state of the first valve element, the hollow pin does not act upon the slot in the closed state, and therefore the duct is closed.

40. The connecting element according to claim 38, wherein, in a loaded state of the first valve element, the hollow pin engages in or reaches through the duct and acts upon or pushes through the slot, and therefore the duct is opened.

* * * * *